United States Patent [19]

Dürr et al.

[11] Patent Number: 4,497,157
[45] Date of Patent: Feb. 5, 1985

[54] PROCESS FOR FILLING PHARMACEUTICAL PRODUCTS CONTAINING PHOSPHOLIPIDES AND HIGHLY VISCOUS AT ROOM TEMPERATURE, INTO HARD CAPSULES

[75] Inventors: Manfred Dürr, Pulheim-Brauweiler; Hans-Ulrich Fribolin, Neuss, both of Fed. Rep. of Germany

[73] Assignee: A. Nattermann & Cie GmbH, Cologne, Fed. Rep. of Germany

[21] Appl. No.: 269,525

[22] Filed: Jun. 2, 1981

[30] Foreign Application Priority Data

Jul. 13, 1980 [DE] Fed. Rep. of Germany ....... 3022136

[51] Int. Cl.³ .......................... B65B 1/20; B65B 55/14
[52] U.S. Cl. ........................................ 53/428; 53/440; 424/37
[58] Field of Search .............. 53/111 RC, 111 R, 127, 53/428, 440, 431; 141/11, 69, 70; 222/190; 604/890–892; 424/36–37; 264/4

[56] References Cited

U.S. PATENT DOCUMENTS

| 2,837,881 | 6/1958 | Schnieder | 53/111 RC |
| 3,126,321 | 3/1964 | Kurtz | 424/37 X |
| 3,780,195 | 12/1973 | Balassa | 424/37 X |

*Primary Examiner*—A. J. Heinz
*Attorney, Agent, or Firm*—Pearne, Gordon, Sessions, McCoy, Granger & Tilberry

[57] ABSTRACT

The present invention is related to a process for filling pharmaceutical products which contain 10 to 98% by weight of a phospholipide and which are highly viscous at room temperature, into hard capsules by admixing to such products a solvent or mixture of solvents in particular amounts, said solvent or solvent mixture having particular evaporation properties, and ejecting the resulting product from a usual filler nozzle under particular conditions, and closing the filled capsule with its cap.

2 Claims, No Drawings

PROCESS FOR FILLING PHARMACEUTICAL PRODUCTS CONTAINING PHOSPHOLIPIDES AND HIGHLY VISCOUS AT ROOM TEMPERATURE, INTO HARD CAPSULES

The present invention is related to a process for filling pharmaceutical products containing 10 to 98% by weight of a phospholipide and which are highly viscous at room temperature, into hard capsules.

Phospholipides, in particular phosphatidylcholine are highly important products due to their therapeutical and food physiological uses. However, phospholipides, in particular phosphatidylcholine represent semisolid products which can be processed only with difficulty and therefor are of considerable disadvantage in this form. When administering the phospholipides, in particular phosphatidylcholine to humans for therapeutical purposes, these products have to be converted into such a form allowing production of galenic products.

Drugs preferably are used in solid form such as powders, pellets, tablets or capsules since in these forms it is simple to exactly dose the products and to safely administer them perorally. However, due to their physical properties such as low flowability and their being oily and tacky products, it is difficult to convert the phospholipide into solid drug materials. These products therefor have to be admixed with the necessary additives and solvents in order to allow administration in the form of solutions, emulsions or suspensions. Since however products in the form of concentrated solutions, emulsions or suspensions cannot be dosed so exactly and are not as stable, they are less suitable then the solid dosage forms. It is therefor highly desirable to convert phospholipid containing products into a solid dosage form, for instance capsules.

Many efforts have been made to fill liquid or viscous products into soft gelatine capsules. The soft gelatine capsule however has the disadvantage that only liquid products may be filled into them having a predominently lipophilic nature since the capsule itself may be destroyed by dissolution in aqueous or alcoholic solutions or may be changed in other undesired ways such as hardening or becoming brittle. Since the product filled into the capsule remains liquid there may occur in the soft gelatine capsule a demixing or sedimentation of the filled product as well as leaker formation at the seam of the capsule. Furthermore, the products to be filled have to have special properties in order to allow a good filling into the soft gelatine capsule wherefor quite often it is not possible to fill highly concentrated and highly viscous products into soft gelatine capsules. Furthermore, the production of soft gelatine capsules is technically very complicated and may be effected only in special machines. Still furthermore there are necessary higher amounts of gelatine for soft gelatine capsules than for hard gelatine capsules.

Therefor, it would represent an improvement to fill such products into hard capsules. Many proposals for the solution of this problem have been made. For instance, pasty and semisolid products have been extruded and pressed into capsules (see German Offenlegungsschrift No. 26 12 472) or have been filled into capsules in the form of thixotropic gels or melts which behave as a liquid during the filling procedure but act as solids within the capsule (see British Patent No. 1892, German Offenlegungsschrift No. 28 38 387, A. CUINE et al., Pharmaz. Industrie 1978, vol. 40, p. 654 to 657).

However, in order to allow a filling of the capsule in an exact amount, the product to be filled should not have too high a viscosity at the filling temperature, has to have a suitable surface tension and should not produce threads during filling. Furthermore, a leakage from the capsule should not occur even after closure of the capsule with its cap without additional measures such as sealing of the capsule.

However, in these processes the viscosity difference between the liquid and the solid phase either is not large enough or the conversion from the liquid into the solid phase is too slow. Furthermore, when using meltable products such products are heated for too long a time in the storage bunkers or bins. Such processes therefor cannot be applied to the filling with high speed filling machines in particular because of thread formation, too long heating in the storage bins and too slow a solidification of the filled products in the capsules.

In another process the products are filled into capsules in the presence of a solvent (see British Patent No. 767 073). The solvent after filling is removed from the filled capsule by evaporation at elevated temperature before the capsule is closed. It is a disadvantage of this process that the lower capsule half has to be kept in a vertical position in the filling machine or in a subsequent part of the machine during the evaporation step until the solvent has been removed. During the evaporation of the solvent there may occur a decomposition of the often sensible active component due to the necessary heating. Furthermore, the solvent to be evaporated may destroy the capsule wall at the temperatures of evaporation. The complete process is quite complicated and therefore may not be carried out with usual filler machines.

It has now been found that products containing phospholipides and highly viscous at room temperature may be readily filled into hard capsules, in particular into hard gelatine capsules, by the following process:

(a) ethanol is added to the highly viscous product in such an amount that a concentrated solution, emulsion or suspension of the product is obtained which is flowable at room temperature or a slightly elevated temperature and under pressure as it is produced for instance by pumps, i.e. in such an amount that the mixed product at this temperature has just a sufficiently low viscosity to be flowable under pressure or a slightly lower viscosity;

(b) this product is now filled into the hard capsule with usual filling machines for the filling of liquids with a heatable filler nozzle, i.e. the product is filled from the nozzle opening arranged in usual distance from the opening of the hard capsule half to be filled, being heated to a temperature close to the boiling point of the ethanol under pressure to the product before ejection from the filler nozzle;

(c) the filled hard capsule half is finally closed in usual manner with the other hard capsule half. The nozzle opening preferably has a diameter of 0.3 to 1.5 millimeters.

Phospholipides useful in the present process are natural as well as synthetic phospholipides. Natural phospholipides (from plants or animals) are in particular phosphatidylcholine, phosphatidylethanolamine, phosphatidylinosite, phosphatidylserine, sphingomyeline, cephaline, lysolecithine, phosphatidylglycol which may be recovered from soya-beans or eggs, and mixtures of such phospholipides, for instance the traded phosphatidylcholines or phosphatidylcholine-mixtures such as Phospholipon ®100: (98% natural phosphatidylcholine from soya-beans)

Phospholipon ®100 H: (98% fully hydrogenated phosphatidylcholine from soya-beans)

Phospholipon ®80: (phospholipides from soya-beans containing 75% phosphatidylcholine and 12% phosphatidylethanolamine).

Synthetic phosphatides are for instance ditridecanoylphosphatidylcholine, dihexandecanoylphosphatidylcholine, dioleylphosphatidylcholine or dilinoylphosphatidylcholine, in particular however dipalmitoylphosphatidylcholine.

Further physiologically active products which may be admixed to the phospholipides are for instance: extracts from plants such as Chelidonium, Crataegus, Curcuma, chestnut, Betula, various berry or Senna extracts; vitamines soluble in fats or water, such as vitamine C, vitamine A, E, F, B-complex of $B_{12}$; ethereal oils such as from fennel, caraway, peppermint, eucalyptus; purines such as theophylline, theobromine or caffeine; alkaloides such as chinidine, ephedrine, codeine, atropine, papaverine, morphines, reserpine, strychnine, ergot alkaloides, in particular ergotamine, ergocristine or ergocornine, raubasine; bile acids such as desoxycholic acid or taurocholic acid; saponines such as escine; hormones such as methyltestosterone or ethinylestrandiole; sulfonamides or antibiotics such as penicillines or cephalosporines; glycosides such as in particular digoxine, digitoxine or strophantine; non-steroidal antirheumatics such as acetylsalicylic acid or indometacine or other pharmaceutical active products.

Pharmaceutically inert carrier materials are in particular the usual pharmaceutical additives such as waxes, hydrated oils, natural, semisynthetical or synthetical triglycerides or mixtures thereof such as cocoa butter and usual suppository products, for instance triglyceride products such as Witepsol ®-suppository products (compare H.P. FIEDLER, Lexikon der Hilfsstoffe für Pharmazie, Kosmetik und angrenzende Gebiete, 1971, vol. 9, pgs. 548 to 550 and 632 to 634); fatty alcohols, solid hydrocarbons such as vaseline or Paraffin solidum; saturated fatty acids such as lauric, myristic, palmitic or stearic acids; emulgators such as ethoxylated triglycerides, polyethoxylated plant oils; fatty acid sugar esters, silicons, gelatine, methylcellulose, hydroxypropoxycellulose, hydroxypropylcellulose, polyethyleneglycol, polyvinylpyrrolidone, polyvinylalcohol, polyacrylic acid and salts thereof.

Useful for the filling in accordance with the present invention are products containing ethanol in an amount corresponding to 0.5 to 10%, in particular 0.5 to 5% of the weight of the highly viscous product.

The mixing proportion of the various components, i.e. the product to be filled, the ethanol and, possibly, usual galenic additives is such that the resulting product has a sufficiently low viscosity for being transported from the storage bunker with usual pumps, a viscosity ranging from 1,000 to 100,000 mPa/sec. at a temperature between 20° and 110° C. In order to guarantee that there does not remain too much ethanol in the product filled into the capsules and that it quickly solidifies in the capsule, there should be added to the highly viscous product only so much ethanol that the resulting product has a viscosity just sufficient for transport under pressure at usual storage temperatures, i.e. at room temperature or slightly elevated temperature, or a slightly lower viscosity at such temperatures.

For producing filled capsules the highly viscous products are converted by the addition of ethanol at low temperature in a storage container in the form of solutions, emulsions or suspensions having a sufficient flowability and are then filled with usual capsule filling machines with means for filling liquids. Useful are for instance ZANASI machines and HÖFLINGER & KARG machines and in particular machines which work at high pressure and with specially controlled valves such as NORDSON & DITTBERNER machines. In these machines, the products are filled with pressure and temperature control by means of a dosing apparatus wherein the products are subjected to elevated temperatures only for a short period of time. When filling the highly viscous products in such a manner there surprisingly does not occur a spraying of the product to be filled nor any evaporation of the solvent with foaming, as it is known from solutions of lecithines in ethanol (see for instance Fette-Seifen-Anstrichmittel 78 (1976) p. 127). However, ethanol is evaporated in such an amount that the filled material momentarily solidifies in the capsule. The degree of evaporation of the ethanol can be controlled in particular by the diameter of the filling nozzle and by the filling pressure, i.e. by the flow speed and thus by the time the product remains between the exit opening of the filling nozzle and the entrance opening of the hard capsule. Most preferred is the application of high pressure since this obviously increases the surface of the product jet during the filling process and thereby increases the evaporation of the ethanol which again causes an increased and more speedy solidification of the product in the capsule. After filling, the filled capsule is closed by adding the upper capsule cap directly, i.e. without any further treatment of the capsule and is taken from the filling machine without danger of leakage.

The capsules may be furthermore provided with a coating resistant to the juices of the stomach. Such coatings are usual natural or synthetic lacquers such as shellac, celluloseacetatephthalate, hydroxymethylcellulosephthalate or acrylic resins such as Eudragit (polyacrylic acids).

The following examples serve to further illustrate the present invention without however limiting the same thereto.

EXAMPLE 1

Phosphatidylcholine: 73 g.

Witepsol W 35: 17 g.

Soya-bean oil: 10 g.

Ethanol: 4 g.

The above products are mixed in a storage vessel with stirring and heating to about 40° C. The resulting solution is filled into capsule by means of a capsule filling machine of the type ZANASI AZ 20 L, the dosage nozzle whereof is heated to 80° C., at a filling speed of 12,000 capsules per hour. The mixture solidifies immediately in the capsule. The capsule is closed by adding its cap thereto and may be removed from the filling machine. The disintigration time of the capsule is determined as described in the test procedure "disintigration of tablets" according to Ph. Eur. III and is below 5 minutes.

EXAMPLE 2

The products of Example 1 are mixed as described in Example 1. They are however filled by means of a filling machine of the type HÖFLINGER & KARG GFK 330 L with the same result.

EXAMPLE 3

Phosphatidylcholine: 73 g.
Witepsol W 35: 17 g.
Soya-bean oil: 10 g.
Ethanol: 2 g.

The products are mixed as described in Example 1 and are filled into capsules using a filling machine of the type HÖFLINGER & KARG GFK 330 with additional equipment for filling liquid products having a compressed-air-controlled magnetic valve, at a filling pressure of about 75 bar. The machine produces 20,000 capsules per hour.

In the same manner as described in Examples 1 to 3 the following mixtures are filled into capsules:

EXAMPLE 4

Phosphatidylcholine: 73 g.
Cetylstearylalcohol: 13 g.
Polyethyleneglycol 400: 10 g.
Cetaceum: 4 g.
Ethanol: 3 g.

EXAMPLE 5

Phosphatidylcholine: 73 g.
Polyethyleneglycol 400: 21.6 g.
Polyethyleneglycol 10 000: 5.4 g.
Ethanol: 3 g.

EXAMPLE 6

Indometacine: 14 g.
Phosphatidylcholine: 63 g.
Witepsol W 35: 14.5 g.
Soya-bean oil: 8.5 g.
Ethanol: 2 g.

EXAMPLE 7

Acetylsalicic acid: 40 g.
Phosphatidylcholine: 40 g.
Witepsol W 35: 13 g.
Soya-bean oil: 7 g.
Ethanol: 5 g.

EXAMPLE 8

7-$\beta$-Hydroxyethyltheophylline: 10 g.
Phosphatidylcholine: 60 g.
Witepsol W 35: 15 g.
Soya-bean oil: 14 g.
DL-$\alpha$-tocopherol: 1 g.
Ethanol: 2 g.

EXAMPLE 9

Hippocastanium extract: 54 g.
Hesperidinmethylchalcon: 13 g.
Phosphatidylcholine: 20 g.
Witepsol W 35: 7 g.
Soya-bean oil: 6 g.
Ethanol: 3 g.

EXAMPLE 10

Dimethylpolysiloxane: 84 g.
Witepsol W 35: 16 g.
Ethanol: 1 g.

EXAMPLE 11

Polyethyleneglycol 20 000: 66.4 g.
Polyethyleneglycol 600: 33.6 g.
Ethanol: 4 g.

EXAMPLE 12

Phosphatidylcholine: 73 g.
Witepsol W 35: 17 g.
Soya-bean oil: 10 g.
Ethylacetate: 7.5 g.

EXAMPLE 13

Phosphatidylcholine: 73 g.
Witepsol W 35: 17 g.
Soya-bean oil: 10 g.
Isopropanol: 4 g.

EXAMPLE 14

Phosphatidylcholine: 73 g.
Witepsol W 35: 16 g.
Soya-bean oil: 10 g.
Cholesterol: 1 g.
Ethanol: 3 g.

EXAMPLE 15

Fully hydrated phosphatidylcholine: 8 g.
Phosphatidylcholine: 65 g.
Witepsol W 35: 16 g.
Soya-bean oil: 10 g.
Ethylacetate: 7 g.

We claim:

1. Process for filling pharmaceutical products which contain 10 to 98% by weight of a phospholipide and which are highly viscous at room temperature into hard gelatin capsules comprising admixing ethylalcohol to the highly viscous product in such an amount that the resulting product at room temperature or slightly elevated temperature has a viscosity just sufficient to allow to transport it by means of pumps, or a slightly lower viscosity, ejecting this resulting product with pressure and with heating prior to ejection from a filler nozzle arranged with its opening opposite to the opening of the hard capsule half to be filled, said heating being sufficient to cause evaporation of ethylalcohol from the resulting product after it is ejected from the filler nozzle, filling the hard capsule half while simultaneously evaporating admixed ethylalcohol as the resulting product is filled into the hard capsule half, and closing the filled hard capsule half with the other hard capsule half, the heating and admixed ethylalcohol content being such that substantially all of the admixed ethylalcohol evaporates between product ejection from the filler nozzle and capsule closing to produce a capsule filling which is substantially solidified and substantially devoid of admixed ethylalcohol.

2. Process according to claim 1 wherein there is used ethanol in an amount corresponding to 0.5 to 10% of the weight of the highly viscous product.

* * * * *

UNITED STATES PATENT AND TRADEMARK OFFICE
CERTIFICATE OF CORRECTION

PATENT NO. : 4,497,157
DATED : February 5, 1985
INVENTOR(S) : Manfred Durr et al.

It is certified that error appears in the above—identified patent and that said Letters Patent is hereby corrected as shown below:

On the title page;

Section [30] Foreign Application Priority Data should read:

-- June 13, 1980 [DE]   Fed. Rep. of Germany............ 3022136 --.

Signed and Sealed this

Twenty-seventh Day of August 1985

[SEAL]

Attest:

DONALD J. QUIGG

Attesting Officer      Acting Commissioner of Patents and Trademarks